US012754181B2

(12) United States Patent
Mao et al.

(10) Patent No.: US 12,754,181 B2
(45) **Date of Patent: *Oct. 6, 2026**

(54) EXTRACTION METHODS FOR EVALUATING SUITABILITY OF A BIOCHEMICAL FILTER

(71) Applicant: Regeneron Pharmaceuticals, Inc., Tarrytown, NY (US)

(72) Inventors: Nathan Mao, Cohoes, NY (US); Annamarie Cruz, East Greenbush, NY (US); Bernhard Schilling, Hudson, NY (US); Scott Carver, Wyantskill, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1126 days.

This patent is subject to a terminal disclaimer.

(21) Appl. No.: 17/804,222

(22) Filed: May 26, 2022

(65) Prior Publication Data

US 2022/0404335 A1 Dec. 22, 2022

Related U.S. Application Data

(63) Continuation of application No. 16/395,431, filed on Apr. 26, 2019, now Pat. No. 11,378,571.

(Continued)

(51) Int. Cl.

*G01N 33/50* (2006.01)
*C12M 1/12* (2006.01)
*G01N 33/58* (2006.01)

(52) U.S. Cl.

CPC ......... *G01N 33/5014* (2013.01); *C12M 37/02* (2013.01); *G01N 33/582* (2013.01)

(58) Field of Classification Search

CPC ............. G01N 33/5014; G01N 33/582; G01N 33/538; C12M 37/02; B01D 15/38

(Continued)

(56) References Cited

U.S. PATENT DOCUMENTS 5,221,483 A 6/1993 Glenn et al.
6,953,686 B1 10/2005 Ramasubramanyan (Continued)

FOREIGN PATENT DOCUMENTS

AU 2008360625 B2 2/2010
CN 1123550 A 5/1996

(Continued)

OTHER PUBLICATIONS

Marchand, G. et al, Endotoxin analysis 2009, Analytical Method 322, 16 pages, downloaded from https://pharesst.irsst.qc.ca/cgi/viewcontent.cgi?article=1009&context=microbiologiques. (Year: 2009).*

(Continued)

*Primary Examiner* — Arlen Soderquist
(74) *Attorney, Agent, or Firm* — Bookoff McAndrews, PLLC

(57) ABSTRACT

Embodiments of the present disclosure include methods and systems for detecting the presence of endotoxins in filters. For example, embodiments of the present disclosure are directed to methods and systems for improving in-process controls by detecting undesirable quantities of endotoxins in filters containing naturally-sourced materials prior to using those filters in the production of formulated drug substances.

19 Claims, 4 Drawing Sheets

Related U.S. Application Data

(60) Provisional application No. 62/665,721, filed on May 2, 2018.

(58) Field of Classification Search
USPC .......................................................... 436/164
See application file for complete search history.

(56) References Cited

U.S. PATENT DOCUMENTS

| | | | | |
|---|---|---|---|---|
| 11,378,571 | B2 * | 7/2022 | Mao | C12M 37/02 |
| 2004/0112832 | A1 | 6/2004 | Sundberg et al. | |
| 2011/0159130 | A1 | 6/2011 | Jain et al. | |

FOREIGN PATENT DOCUMENTS

| | | | |
|---|---|---|---|
| CN | 101351562 | A | 1/2009 |
| CN | 102123777 | A | 7/2011 |
| CN | 105251049 | A | 1/2016 |
| CN | 105492101 | A | 4/2016 |
| CN | 105567672 | A | 5/2016 |
| CN | 106397552 | A | 2/2017 |
| EP | 2321337 | A1 | 5/2011 |
| EP | 2513142 | A1 | 10/2012 |
| FR | 2 840 992 | A1 | 12/2003 |
| KR | 20160013173 | A | 2/2016 |
| TW | 335356 | B | 7/1998 |
| WO | 02/063271 | A2 | 8/2002 |
| WO | 03002731 | A1 | 1/2003 |

OTHER PUBLICATIONS

Uddin, M. S. et al, Journal of Advances in Medical and Pharmaceutical Sciences 2017, 14, 1-17. (Year: 2017).*
Southern, J. A. et al, Journal of Biological Standardization Nov. 1983, 163-170. (Year: 1983).*
Henne, W. et al, Artificial Organs Aug. 1984, 299-305. (Year: 1984).*
Pearson, F. C. et al, Applied and Environmental Microbiology 1984, 48, 1189-1196. (Year: 1984).*
Munson, T. E. et al, Progress in Clinical and Biological Research 1985, 189, 211-220. (Year: 1985).*
Richards, C. et al, Journal of Clinical Pharmacy & Therapeutics 1990, 15, 53-58. (Year: 1990).*
Milton, D. K. et al, American Industrial Hygiene Association Journal 1990, 51, 331-337. (Year: 1990).*
Roslansky, P. F. et al, Journal of Clinical Microbiology 1991, 29, 2477-2483. (Year: 1991).*
Anderson, J. et al, Cytotherapy Apr. 2002, 557-559. (Year: 2002).*
Usami, M. et al, Blood Components 2002, 42, 1189-1195. (Year: 2002).*
Nagasawa, K. et al, Journal of Artificial Organs Jun. 2003, 49-54. (Year: 2003).*
Li, J. et al, Journal of Chromatography B 2003, 791, 55-61. (Year: 2003).*
Ohata, A. et al, Artificial Organs 2003, 27, 729-735. (Year: 2003).*
Finkelman, M. A., LAL Update 2005, 22, 1-4 (Year: 2005).*
3M Filtration CUNO Product Brochure 2007, 8 pages. (Year: 2007).*
Buchacher, A. et al, PDA Journal of Pharmaceutical Science and Technology 2010, 64, 536-544. (Year: 2010).*
Shogren, E. et al, Journal of Environmental Monitoring 2011, 13, 1082-1087. (Year: 2011).*
Riedman, D. et al, BioProcess International 2011, Supplement 28-35. (Year: 2011).*
Nordli, H. R. et al, Carbohydrate Polymers 2016, 150, 65-72. (Year: 2016).*
Wong, J. et al, PLOS One 2016, 11, paper e0164978, 16 pages. (Year: 2016).*
Vigor, K. et al, Biotechnology Progress 2016, 32, 1494-1502. (Year: 2016).*
Liu, J. et al, Carbohydrate Polymers 2017, 172, 11-19. (Year: 2017).*
Liu, J. et al, Biomacromolecules 2018, 19, 150-157. (Year: 2018).*
"Customer Application Brief: Filtration of Cell Culture Growth Media and Process Buffers" 3M Purification Inc., Jan. 1, 2011 (7 pages).
Journal of Pharmaceutical Science)), Microbiological Methods for Quality Control of Membrane Filters, Bowman, 222-225 (4 pages).
AmericanBio (Phosphate Buffered Saline Solution, AmericanBio, 2020 (Year: 2020).
Bowman et al (Microbiological Methods for Quality Control of Membrane Filters, Journal of Pharmaceutical Sciences, 1967, vol. 56, No. 2, pp. 222-225 (Year: 1967).
Dawson, Mick, Endotoxin Limits for Parenteral Drug Products, BET White Paper vol. 1, No. 2 (Apr. 2017) (7 pages).
FDA (Chapter. Bacterial Endotoxins and Pyrogens, Inspection Technical Guides, 2014, 9 pages) (Year: 2014).
GE Healthcare Life Sciences Handbook, "Design of Experiments in Protein Production and Purification," Jan. 1, eo15 (128 pages).
Hou et al., "Depyrogenation by Endotoxin Removal with Positively Charged Depth Filter Cartridge," Journal of Parental Science and Technology, Parental Drug Association, vol. 44. No. 4, Jul.-Aug. 1990, pp. 204-209 (6 pages).
International Search Report in corresponding Application No. PCT/US2019/029268 mailed Oct. 18, 2019 (7 pages).
Kashiwagi et al., "The Performance Evaluation of Endotoxin Retentive Filters in Haemodialysis," Journal Nippon Medical School, Jan. 1, 2011; 78 (4), pp. 214-223 (10 pages).
Michen, Benjamin, et al., Removal of colloidal particles in ceramic depth filters based on diatomaceous earth, Separation and Purification Technology 81.1 (2011): 77-87 (11 pages).
Obrien et al (Large-Scale, Single-Use Depth Filtration Systems, BioProcess International, 2012, 14 pages) (Year: 2012).
O'Brien et al., "Evaluation of Endotoxin Retention by Adsorptive-Based Filtration Media," PDA Journal of Pharmaceutical Science and Technology, vol. 61, No. 2, Mar.-Apr. 2007, pp. 75-87 (13 pages).
Office Action issued in Chinese Application CN201980028426.9 on Dec. 14, 2021 (10 pages).
Pall Corporation, "Validation Guide: Mustang E Membrane Chromatography Capsules," Aug. 17, 2017, pp. 1-11, available online at https://biotech.pall.com/content/dam/pall/biopharm/lit-library/gated/Validation&20Guides/09.3092_USTR2267_Mustang_E_VG_EN (11 pages).
Search Report issued in Chinese Application No. CN201980028426.9 (2 pages).
Vanhaecke et al., "Endotoxin Removal by End-Line Filters," Journal of Clinical Microbiology, Dec. 1, 1989, pp. e710-2712 (3 pages).
Office Action for Taiwanese Application No. 108113294, Jan. 11, 2023, 5 pages.

* cited by examiner

300

EXTRACTION METHODS FOR EVALUATING SUITABILITY OF A BIOCHEMICAL FILTER

CROSS-REFERENCE TO RELATED APPLICATION(S)

This application is a continuation under 37 CFR § 1.53 (b) of U.S. application Ser. No. 16/395,431 filed on Apr. 26, 2019, issued as U.S. Pat. No. 11,378,571, which claims priority to U.S. Provisional Application No. 62/665,721, filed May 2, 2018, each of which is incorporated by reference herein in its entirety.

TECHNICAL FIELD

Aspects of the present disclosure relate generally to filtration screening systems and methods, and, specifically, to embodiments of methods and systems for improving processes by screening filters for presence of toxins, such as endotoxins, and/or washing endotoxins from filters.

BACKGROUND

Control of bacterial endotoxins is important in biologics drug production and manufacturing, as endotoxins can cause complications in patients (e.g., eliciting an immune response, causing sepsis and/or septic shock, etc.). Endotoxins may include lipopolysaccharides (LPS) found in the outer membrane components of gram-negative bacteria, which may be released during, e.g., cell growth, cell lysis, or cell death. LPS include a lipid component, lipid A (which may cause endotoxicity); an oligosaccharide core, and a heteropolysaccharide chain (0-antigen). 0-antigens include repeating oligosaccharides which may vary with bacterial strain and/or serotype. LPS are hydrophobic due to their lipid tails, and have a net negative charge in slightly acidic to basic pH. The combination of the hydrophobic and negatively charged characteristics in LPS can cause LPS to bind to many different types of molecules through various modes of interaction.

Preparation of biologic drug products may include various filtration processes. In some cases, filtration processes may include the use of naturally-sourced raw materials (e.g., filters containing cellulose fibers, diatomaceous earth (DE), and/or charge modification resins). Harvest depth filters, for example, which may be used to remove cell debris and colloids from cell culture fluid, may include materials sourced from plants, animals, and mineral deposits. These filters have the potential to introduce endotoxins into biologics preparation processes. Suppliers and/or vendors of naturally-sourced raw materials, such as these filters, may perform processes to regulate and/or reduce endotoxins within their products. Suppliers and/or vendors may also provide endotoxin specifications along with their products (e.g., identifying a maximum acceptable or tolerable quantity or concentration of endotoxins in their products). However, these specifications may be inexact, and in some cases, the endotoxin specifications for naturally-sourced raw materials may be different from (e.g., less strict than) the requirements of the users of those materials (e.g., the requirements for manufacturing a biologic drug product).

Biologic drug product manufacturers and/or distributors may use naturally-sourced raw materials (e.g., filters having naturally-sourced components) to prepare biologics, and may have their own established processes to detect and/or remove endotoxins from biologic drug products. For example, regulatory requirements (provided by a regulatory body such as the U.S. Food and Drug Administration) may include specifications that drug products distributed within their jurisdictions must meet. Moreover, manufacturer in-process controls (IPCs) for a drug product may include additional standards and protocols to ensure that regulatory requirements are met and/or surpassed. For example, a manufacturer's IPC may require testing each batch of a prepared formulated drug substance for the presence and/or quantity of endotoxins, and discarding contaminated batches. While such protocols improve the safety of drug products, discovering endotoxin contamination at this late stage in the manufacturing process may disadvantageously result in the loss of large quantities of formulated drug substance and/or active ingredients.

The systems and methods disclosed herein may improve the efficiency and/or productivity of drug product manufacturing methods and systems, and may address one or more problems identified above.

SUMMARY

Embodiments of the present disclosure may be directed to a method for evaluating suitability of a plurality of filters for use in a biologic purification process, each of the plurality of filters including a naturally-sourced material. The method may include selecting a filter from the plurality of filters, passing a volume of a buffer solution through the selected filter, wherein the buffer solution has a conductivity of at least about 40 mS/cm at 25° C. when tested in accordance with ASTM D1125, performing an assay to detect a presence of an endotoxin in the buffer solution, evaluating the suitability of the plurality of filters for use in the cell culture process based on a result of the assay, and repeating the selecting, passing, performing, and evaluating steps at periodic time intervals. In some embodiments, the evaluating step may include at least one of approving the plurality of filters for use in the biologic purification process if a quantity of endotoxin in the buffer solution is below a predetermined threshold, or rejecting the plurality of filters for use in the biologic purification process if the quantity of endotoxin in the buffer solution is above a predetermined threshold.

Some embodiments of the present disclosure may include a method for detecting the presence of an endotoxin. The method may include contacting a naturally-sourced material with a buffer solution, wherein the naturally-sourced material includes cellulose, and wherein the buffer solution has a conductivity of at least about 40 mS/cm at 25° C. when tested in accordance with ASTM D1125, and performing an assay on the buffer solution to detect the endotoxin in the buffer solution.

In some embodiments, the method may include, after contacting the naturally-sourced material with the buffer solution, contacting the naturally-sourced material with a cell culture fluid. In some embodiments, the buffer solution may be configured to disrupt one of an electrostatic interaction or a hydrophobic interaction between the endotoxin and the naturally-sourced material. In some embodiments, the buffer solution may comprise one of tris(hydroxymethyl) aminomethane, phosphate, citrate, histidine, or arginine. The step of contacting the naturally-sourced material with a buffer solution may include, for example, passing at least 25 $L/m^2$ of the buffer solution through a filter that comprises the naturally-sourced material. In some embodiments, the method may include, after contacting the naturally-sourced material with the buffer solution, contacting the naturally-sourced material with water for injection (WFI) and performing an assay on the WFI to detect the endotoxin(s) in the WFI. In some embodiments, the assay may be one of a Limulus amebocyte lysate (LAL) assay or a fluorescent assay.

Further embodiments of the present disclosure may include methods for determining suitability of a buffer solution for use in an endotoxin detection process. The methods may include passing the buffer solution through a first filter of a filter lot, the filter lot including a plurality of filters including naturally-sourced materials, wherein the buffer solution is configured to disrupt one of an electrostatic interaction or a hydrophobic interaction between the endotoxin and the first filter, assaying the buffer solution to detect a quantity of the endotoxin present in the buffer solution, passing a cell culture fluid through a second filter of the filter lot, assaying the cell culture fluid to detect a quantity of the endotoxin present in the cell culture fluid, comparing the quantity of the endotoxin detected in the buffer solution to the quantity of the endotoxin detected in the cell culture fluid.

In some embodiments, the naturally-sourced materials may comprise cellulose, diatomaceous earth, or a combination thereof. In some embodiments, assaying the cell culture fluid comprises assaying a clarified pool of the cell culture fluid. Further, for example, the method may include determining a threshold quantity of endotoxin based on the quantity of the endotoxin detected in the cell culture fluid, and if the quantity of the endotoxin detected in the buffer solution is above the threshold, approving the buffer solution for use in the endotoxin detection process.

Further embodiments of the present disclosure may include a method for washing endotoxins from a filter including naturally-sourced materials. The method may include passing at least 25 L/m$^2$ of a buffer solution through the filter, wherein the buffer solution has a conductivity of at least about 40 mS/cm at 25° C. when tested in accordance with ASTM D1125.

In some embodiments, the method may include, after passing the buffer solution through the filter, passing a volume of cell culture fluid through the filter. In some exemplary embodiments, the buffer solution comprises sodium phosphate at a concentration of about 10 mM.

BRIEF DESCRIPTION OF THE DRAWINGS

The accompanying drawings, which are incorporated in and constitute a part of this specification, illustrate exemplary embodiments, and together with the description, serve to explain the principles of the disclosed embodiments. In the drawings.

DETAILED DESCRIPTION

Figure 1:
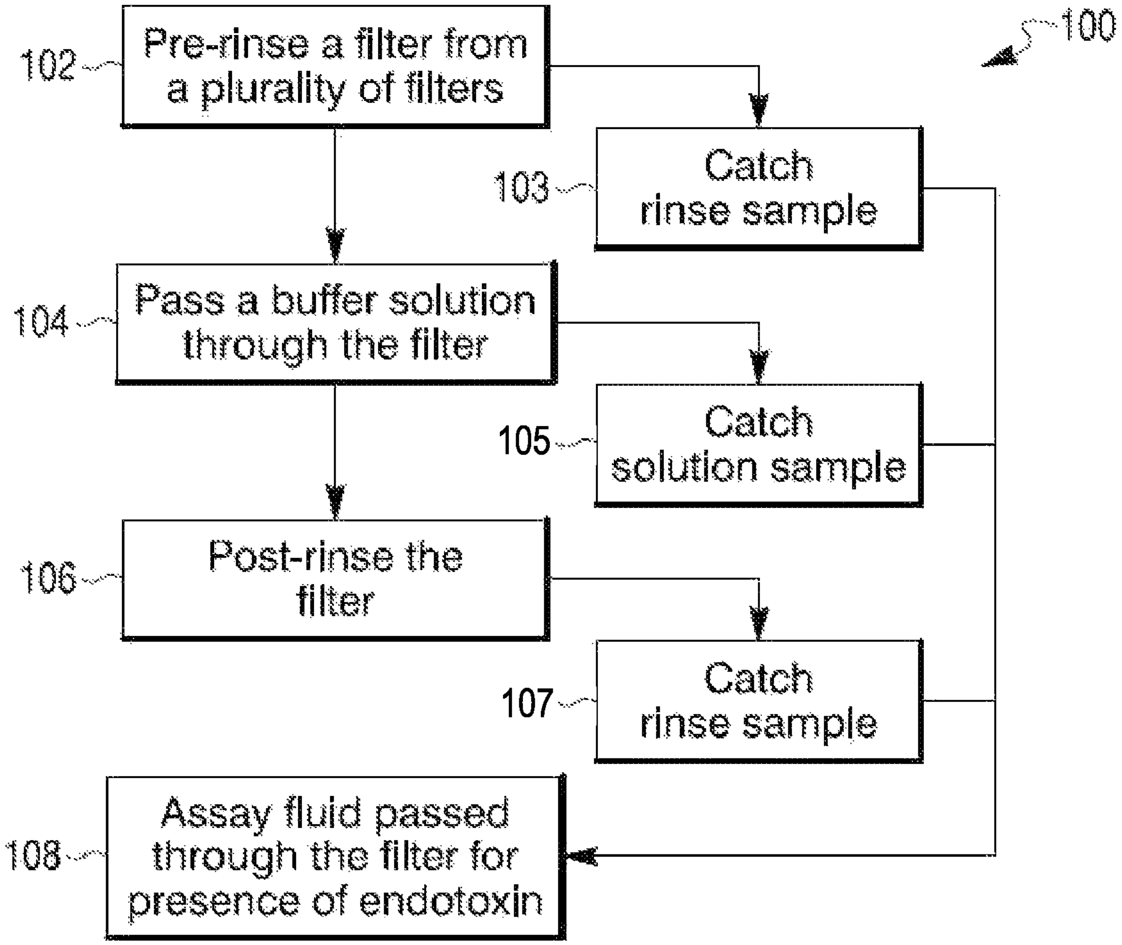
FIG. 1 depicts, in flow-chart form, an exemplary process for evaluating the suitability of a plurality of filters for use in a biologic purification process, according to the present disclosure.

The present disclosure relates to improvements in drug product manufacturing and purification processes, as well as improvements to in-process controls related to drug product manufacturing and purification processes. In particular, aspects of the present disclosure relate to filtration systems, and to methods and systems for detecting toxins in, and/or removing toxins from, filters containing naturally-sourced materials.

While the present disclosure is written with respect to detection or control of endotoxins, the systems and methods disclosed herein may be applicable to other leachables present in filtration materials or other raw materials, such as beta-glucans.

Filters containing naturally-sourced materials, such as some harvest depth filters, can pose a risk to biologic drug manufacturing processes. For example, such filters can introduce endotoxins into the processes during operation of the harvest unit. Control of endotoxin levels in depth filters may be challenging since, as discussed above, their components are often sourced from plants, animals, and/or mineral deposits that can contain toxins. Formulated drug substances prepared using filters that include naturally-sourced materials may be tested for the presence of endotoxins, but, as previously discussed, detection of endotoxins at a later stage of drug product development may disadvantageously result in the expensive loss of batches of drug substance or active ingredient. In some cases, depth filters may be screened and/or cleaned using, e.g., a wash of mammalian cell culture fluid (CCF). CCF may be an effective endotoxin screening tool. For example, because CCF is a complex mixture comprising molecules that have a range of charges and hydrophobicities, CCF may be capable of binding to, and extracting, a variety of contaminants from depth filters. However, a single depth filter requires a high volume of CCF (e.g., at least about 100 L/m$^2$) to be effectively screened, and using CCF to determine presence of an endotoxin, instead of using that CCF as a source of an active ingredient, may thus be expensive and wasteful—especially if multiple filters must be screened to determine whether a group of depth filters is suitable for use. Moreover, CCF and filters through which CCF have been passed typically are not storable for long periods of time, due to a risk of microbial growth in the cell culture. Thus, the use of CCF to determine the presence of endotoxin in a filter may limit the time window during which the filter may be usable.

Described herein are endotoxin screening procedures that have been developed using buffer solutions that can act as a surrogate for CCF in terms of displacing endotoxin presence in the depth filters which, in turn, can contaminate the resulting clarified harvest pool.

Unless otherwise defined, all technical and scientific terms used herein have the same meaning as is commonly understood by one of ordinary skill in the art to which this invention belongs. The materials, methods, and examples are illustrative only and not intended to be limiting. One of ordinary skill in the art will appreciate that routine variations on the disclosed materials, methods, and examples are possible without undue experimentation. All publications, patent applications, patents, sequences, database entries, and other references mentioned herein are incorporated by reference in their entirety. In case of conflict, the present specification, including definitions, will control.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." For such terms, and for the terms "for example" and "such as," and grammatical equivalences thereof, the phrase "and without limitation" is understood to follow unless explicitly stated otherwise. As used herein, the term "about" and the signifier "—" are meant to account for variations due to experimental error. All measurements reported herein are understood to be modified by the term "about," whether or not the term is explicitly used, unless explicitly stated otherwise. The term "about" is understood to encompass+/−10% of the referenced value. As used herein, the singular forms "a," "an," and "the" include plural referents unless the context clearly dictates otherwise. Moreover, in the claims, the recited values, limits, and/or other ranges mean the respective value, limit, and/or range+/−10%.

As used herein, the term "antibody" includes full antibodies (e.g., full antigen-binding molecules) as well as antigen-binding fragments of full antibody molecules. Full antibodies may include, e.g., antibodies of any isotype (IgA, IgD, IgG, IgE, IgM, etc.) and any subclass (e.g., IgG 1, 2, 3, or 4). Full antibodies may have molecular weights of, e.g., at least about 100 kDa, such as at least about 110 kDa, about 120 kDa, about 130 kDa, about 140 kDa, or about 150 kDa. The terms "antigen-binding portion" of an antibody, "antigen-binding fragment" of an antibody, and the like, as used herein, include any naturally occurring, enzymatically obtainable, synthetic, or genetically-engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, also are encompassed within the expression "antigen-binding fragment," as used herein.

As used herein, the term "biologic" may refer to a large molecule (e.g., having a size greater than 30 kDa) created in a living system such as a cell. Biologics may include proteins (e.g., antibodies), nucleic acids, large sugars, etc. Unlike small molecules that may have well-defined chemical structures, biologics may have highly complex structures that cannot be easily quantified by laboratory methods. Thus, it may be desirable to achieve purity, consistency, and quality in the manufacturing of biologics to ensure biologic quality, especially when intended for medical use.

As used herein, the term "filter" may refer to a filter for use in one or more stages of preparing a drug product containing a protein, such as cell culture clarification, protein separation, etc. A filter may include one or more naturally-sourced and/or synthetic materials, such as plastics or other polymers, metals, resins, minerals, and the like. While much of the present disclosure is provided in the context of screening filters containing naturally-sourced materials for endotoxins prior to using use such filters in biologic preparation processes, it is contemplated that the systems and methods disclosed herein may apply to a wide variety of filters.

As used herein, the term "depth filter(s)" (also called "harvest depth filter(s)") may refer to a filter or filters comprising one or more naturally-sourced materials, such as cellulose fibers, diatomaceous earth (DE), and/or charge modification resins. Multiple layers of filter media sheets made from one or more of these and/or other materials may be stacked to form a depth filter. Depth filters may be used in, e.g., clarification of cell cultures, such as mammalian Chinese hamster ovary (CHO) cell cultures, during preparation of a biologic. The manufacture of depth filters may, in some instances, be performed in stringent microbial-controlled environments. Depth filters may be configured to filter or separate various types of particles. For example, some depth filters may be designed to have a positive charge, in order to better facilitate removal of negatively-charged species such as, e.g., cell debris, host cell DNA, and/or host cell proteins in a biologic purification process. As an example, a depth filter may include layers of cellulose pulp matrices and charge modification resins.

As used herein, the term "drug product" may refer to a volume of a formulated drug substance apportioned into a primary packaging component for packaging, transportation, delivery, and/or administration to a patient. Drug products may include one or more active ingredient(s) or drug(s), including, e.g., biologics.

As used herein, the term "active ingredient" or "drug" may refer to a small molecule, a peptide, or a polypeptide, such as an antibody. In some embodiments, for example, the term "drug" or "active ingredient" may refer to a vascular endothelial growth factor (VEGF) derivative. In other aspects, the term "drug" or "active ingredient" may refer to aflibercept, which is described in one or more of U.S. Pat. Nos. 7,070,959, 7,303,746, 7,303,747, 7,306,799, 7,374,757, 7,374,758, 7,531,173, 7,608,261, 7,972,598, 8,029,791, 8,092,803, 8,343,737, and 8,647,842, each of which is incorporated by reference herein in its entirety.

In some aspects, the term "drug" or "active ingredient" may refer to an antibody. In some aspects, the term "drug" or "active ingredient" may refer to alirocumab, which is described in U.S. Patent Application Publication Nos. 2014/0356371 and 2014/035670, each of which is incorporated by reference in its entirety. In another aspect, the term "drug" or "active ingredient" may refer to sarilumab, which is described in U.S. Patent Application Publication Nos. 2016/0152717, 2014/0302053, and 2013/0149310, each of which is incorporated by reference in its entirety. In another aspect, the term "drug" or "active ingredient" may refer to dupilumab, which is described in U.S. Patent Application Publication No. 2014/0356372, which is incorporated by reference herein in its entirety. In another aspect, the term "drug" or "active ingredient" may refer to one or more of the group consisting of evolocumab, bevacizumab, ranibizumab, tocilizumab, certolizumab, etanercept, adalimumab, abatacept, infliximab, rituximab, anakinra, trastuzumab, pegfilgrastim, interferon beta-1a, Insulin glargine [rDNA origin] injection, epoetin alpha, darbepoetin, filigrastim, and golimumab.

As used herein, the term "raw materials" may refer to materials or components involved in drug product manufacturing (e.g., starting materials, filters, reagents, solvents, etc.). The term "naturally-sourced materials" may refer to materials or components sourced from plants, animals, or mineral deposits. And, as used herein, the term "naturally-sourced raw material(s)" may refer to raw material(s) sourced, fully or in part, from plants, animals, or mineral deposits. For example, some harvest depth filters and depth filter media may be naturally-sourced raw materials, as they may include materials derived from plants, animals, or mineral deposits (e.g., cellulose fibers, diatomaceous earth, etc.) Naturally-sourced raw materials may vary somewhat in quality and/or contents over time due to variability in their natural sources. Naturally-sourced raw materials may include materials derived from natural sources that have undergone one or more physical processes such as, e.g., grinding, milling, cutting, weaving, etc.

As discussed above, there exists a need to improve biologic purification and preparation processes, particularly with regards to endotoxins that may be present due to, e.g., naturally-sourced materials used in depth filters during the purification and preparation processes. Systems and methods disclosed herein may allow for screening of filters and/or lots of filters (such as depth filters) for endotoxins prior to use of the filters in biologic preparation processes, thus enabling the removal or cleaning of filters with undesirable amounts of endotoxins before endotoxins in those filters contaminate batches of formulated drug product.

Reference will now be made in detail to the exemplary embodiments of the present disclosure described below and illustrated in the accompanying drawings. Wherever possible, the same reference numbers will be used throughout the drawings to refer to same or like parts.

Figure 2:
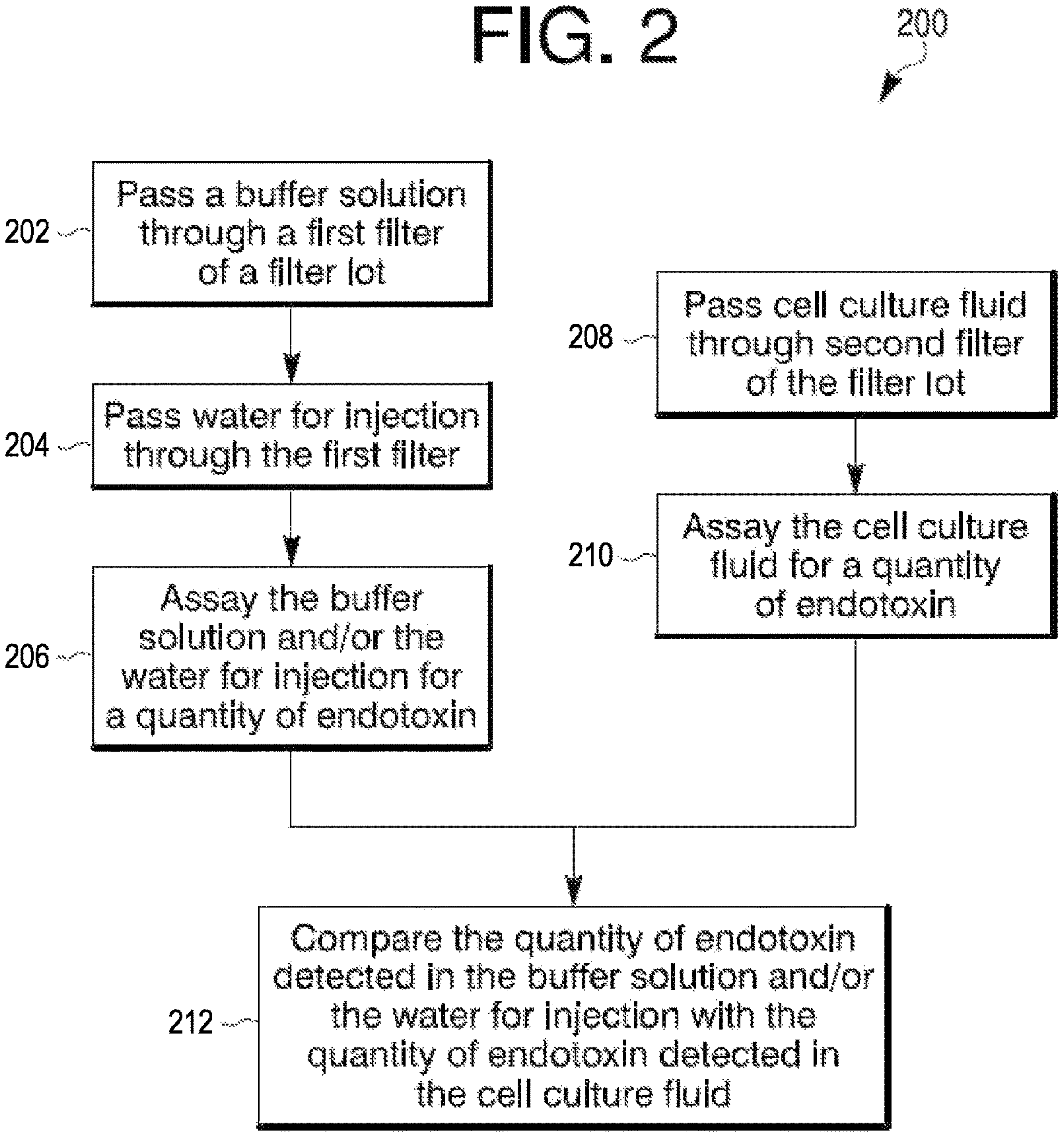
FIG. 2 depicts, in flow-chart form, an exemplary process for determining suitability of a buffer solution for use in an endotoxin detection process according to the present disclosure.

FIGS. 1 and 2 depict, in flow chart form, processes according to some aspects of the present disclosure. While they are described separately below, details of one process described herein may be applicable to one or more other processes described herein, and vice versa. The processes described in FIGS. 1 and 2 are merely exemplary, and it will be apparent to those of ordinary skill in the art that steps from these processes may be repeated or omitted. Depicted steps may be performed in or out of sequence, and one or more steps may be performed simultaneously. Moreover, the addition of more steps to these processes may be within the purview of those of ordinary skill in the art.

FIG. 1 depicts, in flow-chart form, an exemplary process 100 for evaluating the suitability of a plurality of filters for use in a biologic purification process, according to the present disclosure. According to step 102, a filter from a plurality of filters may be pre-rinsed with a suitable liquid. According to step 103, a rinse sample may be caught (e.g., obtained or retrieved) from the liquid that has passed through the filter. According to step 104, a buffer solution may be passed through the filter. According to step 105, a sample of the solution may be caught from the solution that has passed through the filter. According to step 106, the filter may be post-rinsed, e.g., with the same type of liquid of step 102 or another suitable liquid. According to step 107, a post-rinse sample may be caught from the liquid that has passed through the filter. According to step 108, the caught samples of fluid (per steps 103, 105, and/or 107) passed through the filter (per steps 102, 104, and/or 106) may be assayed for the presence of endotoxin. Each sample may be assayed separately in the sequence in which it is received, or multiple samples may be analyzed simultaneously.

According to step 102, a filter from a plurality of filters may be pre-rinsed. The plurality of filters may be any group of filters that potentially contain endotoxins. For example, the plurality of filters may be a batch, lot, or other group of filters that have been manufactured in a similar time or place, or using similar materials or sources of materials. In some embodiments, a common source, time of manufacture, and/or place of manufacture of the plurality of filters may be identifiable by, e.g., a lot number or other identifying information. In further embodiments, the plurality of filters may be identified, sold, or shipped as a group by a filter manufacturer, supplier, or distributor. In some embodiments, each of the plurality of filters may include naturally-sourced materials. In some embodiments, the filters may be harvest depth filters.

The filter from the plurality of filters may be a representative filter from the plurality of filters. In some embodiments, the filter may be randomly selected from the plurality of filters. In some embodiments, more than one filter from the plurality of filters may be evaluated according to the steps of process 100. For example, two, three, four, or five or more filters from the plurality of filters may be evaluated through the steps of process 100. In some embodiments, a number of filters may be selected from the plurality of filters in order to gain a representative sample of the plurality of filters.

The filter from the plurality of filters may be pre-rinsed with any suitable rinsing fluid. Rinsing may include, e.g., installing the filter in an appropriate filtration apparatus and contacting the filter with a volume of a fluid. For example, a harvest depth filter may be installed in a harvest depth apparatus, and a volume of rinsing fluid may be passed through the harvest depth filter. The rinsing fluid may be any suitable fluid able to remove loose particles, debris, and/or other contaminants from the filter. In some embodiments, the rinsing fluid may be or comprise purified water, such as water for injection (WFI).

Any suitable volume of rinsing fluid may be used to pre-rinse the filter. In some embodiments, a volume of rinsing fluid may be determined based on the size (e.g., cross-sectional size and length) and/or porosity of the filter, and an estimated volume of fluid sufficient to remove loose particulates from the filter. For example, the volume of rinsing fluid may be selected based on a surface area of the filter (e.g., $L/m^2$). In some embodiments, at least about 20 $L/m^2$ of rinsing fluid may be used to pre-rinse the filter. In some embodiments, between about 50 $L/m^2$ and about 150 $L/m^2$ of pre-rinsing fluid may be used. In some embodiments, at least about 25 $L/m^2$, about 50 $L/m^2$, about 75 $L/m^2$, about 100 $L/m^2$, about 125 $L/m^2$, or about 150 $L/m^2$ of rinsing fluid may be used.

According to step 103, a rinse sample may be caught (e.g., retrieved or obtained). The rinse sample may comprise, for example, a volume of rinsing fluid that has been used to pre-rinse the filter. For example, in an embodiment in which pre-rinsing the filter includes passing the rinsing fluid through the filter, a rinse sample may be caught from the rinsing fluid that has passed through the filter. In some embodiments in which the filter has been installed in an apparatus (e.g. a harvest depth filter apparatus), a rinse sample may be caught via an outlet of the apparatus.

The rinse sample may be any volume of rinsing fluid suitable for assaying for a presence or quantity of endotoxin. For example, if step 108 of process 100 includes performing a LAL assay (e.g., LAL kinetic turbidimetric assay (KTA)), the rinse sample may comprise at least an amount of rinsing fluid suitable for performance of that assay.

In some embodiments, according to step 103, multiple rinse samples may be caught, e.g., periodically during the pre-rinse step. For example, 2, 3, 4, 5, or 6 different rinse samples may be caught. In an instance in which the pre-rinse step includes at least about 60 L/m$^2$ or about 75 L/m$^2$ of rinsing fluid, for example, rinse samples of suitable volumes may be caught at, e.g., 15 L/m$^2$, 20 L/m$^2$, 25 L/m$^2$, 30 L/m$^2$, or 50 L/m$^2$ intervals.

According to step 104, a buffer solution may be passed through the filter. Without intending to be bound by theory, it is believed that certain buffer solutions may have physical and/or chemical properties that allow the buffer solutions to disrupt interactions between the filter and endotoxins that may be bound to, or otherwise incorporated into, the filter.

For example, negatively-charged endotoxins may be bound to a positively-charged filter matrix via an electrostatic interaction. The buffer solution may thus have a conductivity or another property suitable for disrupting the electrostatic interaction between at least a portion of the endotoxins and the filter, allowing the endotoxin(s) to be washed out with the buffer solution. Without intending to be bound by theory, anions in the buffer solution may bind with the endotoxins, for example, displacing the endotoxins from the filter media and allowing for the removal of the endotoxins from the filter media with the buffer solution. In some embodiments, for example, a suitable buffer solution may have a conductivity of at least about 5 mS/cm, at least about 10 mS/cm, at least about 15 mS/cm, at least about 20 mS/cm, at least about 25 mS/cm, at least about 30 mS/cm, at least about 35 mS/cm, at least about 40 mS/cm, at least about 45 mS/cm, at least about 50 mS/cm, at least about 55 mS/cm, or at least about 60 mS/cm, such as between about 20 mS/cm and about 60 mS/cm, between about 30 mS/cm and about 55 mS/cm, between about 30 mS/cm and about 40 mS/cm, or between about 40 mS/cm and about 50 mS/cm.

As another example, the buffer solution may have physical and/or chemical characteristics that allow the buffer solution to disrupt hydrostatic interactions between endotoxins and the filter. In some embodiments, the buffer solution may comprise a monovalent salt and/or a divalent salt. For example, the buffer solution may comprise, for example, sodium chloride. In some embodiments, the buffer solution may comprise potassium, magnesium, or calcium ions. In some embodiments, the buffer solution may exhibit an approximately even hydrophilic/lipophilic balance. In some embodiments, the buffer solution may comprise tris (hydroxymethyl)aminomethane (Tris), a phosphate (e.g., sodium phosphate), a citrate, histidine, arginine, or a mixture thereof. An exemplary pH of the buffer solution may be between about 5.5 and about 8.8, such as between about 5.5 and about 6.0, between about 6.0 and about 8.0, or between about 6.5 and about 7.5.

As with step 102, any suitable volume of buffer solution may be passed through the filter. In some embodiments, the volume of buffer solution may be determined based on the size of the filter and/or the volume and/or type of pre-rinse rinsing fluid used prior to introduction of the buffer solution. In some embodiments, at least about 20 L/m$^2$ of buffer solution may be passed through the filter. In some embodiments, between about 50 L/m$^2$ and about 150 L/m$^2$ of buffer solution may be used. In some embodiments, at least about 25 L/m$^2$, about 50 L/m$^2$, about 75 L/m$^2$, about 100 L/m$^2$, about 125 L/m$^2$, or about 150 L/m$^2$ of buffer solution may be used.

According to step 105, a sample of the buffer solution may be caught. This may be performed in any suitable method, such as any method described with respect to step 103. According to step 106, the filter may be post-rinsed. A post-rinse may be performed in any suitable method, such as any method described with respect to step 102. As with step 102, the post rinse fluid may be or comprise, e.g., WFI.

According to step 107, a post-rinse sample may be caught. This may be performed in any suitable method, such as any method described with respect to steps 103 and 105.

According to step 108, the caught samples of fluid passed through the filter may be assayed for the presence of endotoxins. As mentioned previously, samples caught throughout process 100 may be of a sufficient volume to be assayed for the presence of endotoxins. In some embodiments, the assay(s) may only test for a presence (or absence) of endotoxin. In further embodiments, both a presence and a quantity of endotoxin may be determined. Any suitable assay, now known or future developed, may be used to determine the presence and/or quantity of endotoxins. For example, a LAL assay (or LAL-based assay), a fluorescent assay, or a recombinant factor C assay may be used. In some embodiments, a LAL KTA is used. In some embodiments, a LAL KTA with beta-glucan blockers may be used.

In some embodiments, only a sample or samples of the buffer solution and the post-rinse fluid may be caught and/or assayed for the presence of endotoxins, as opposed to a sample or samples of the pre-rinse fluid, the buffer solution, and the post-rinse fluid. In some embodiments, only a sample or samples of the buffer solution may be caught and/or assayed for the presence of endotoxins.

In some aspects, systems and methods disclosed here may be used for repeated periodic screening of filters. For example, process 100 may be implemented at regular or irregular intervals, such as when a plurality of filters are received from a new vendor, a new lot or batch is manufactured, and/or filters that include new naturally-sourced materials are made. In some embodiments, for example, one part (or all) of process 100 may be repeated weekly, biweekly, monthly, or quarterly with a different plurality of filters.

In some aspects, systems and methods disclosed herein may be implemented along with an alert or action system. For example, the detection of more than a predetermined threshold of endotoxin in a sample of buffer solution passed through a filter may trigger an alert. An alert may be, e.g., a digital alert implemented as a part of a computer program associated with data collection during the screening process, or may be an analog alert triggered by visual interpretation of the data from an assay. Alerts may include suggested courses of action, such as screening an additional filter selected from the same plurality of filters as an already-screened filter. For example, steps 102-108 of process 100 may be repeated with one or more additional filters from the plurality of filters due to an alert triggered by performing steps 102-108 with a first filter from the plurality of filters.

Additionally or alternatively, the detection of more than a predetermined threshold of endotoxin in a sample of buffer solution passed through a filter may trigger more drastic action(s), such as cleaning, destroying, or discarding the filter, or cleaning, destroying, or discarding the plurality of filters associated with the filter. In some aspects, cleaning the filter, or the plurality of filters associated with the filter, may include passing a volume of buffer solution through the filter or plurality of filters. In further aspects, cleaning the filter or plurality of filters may include passing a volume of cell culture fluid through the filter or plurality of filters, and then discarding that volume of cell culture fluid. In some aspects, the processes herein may include generating or keeping a record of filter screenings performed using process 100.

Alerts and/or actions may be triggered based solely on the presence of endotoxin in an assayed sample, or may be triggered based on a predetermined threshold quantity of endotoxin in an assayed sample. Such a threshold quantity (or quantities) may depend on a variety of factors, such as the type of drug product being manufactured, the active ingredient being filtered, regulations internal to a manufacturer, or regulations external to a manufacturer or distributor (e.g., national or international regulations). For example, in some embodiments, alerts may be triggered by an endotoxin quantity of at least about 0.05 EU/mL, at least about 0.07 EU/mL, at least about 0.09 EU/mL, at least about 0.10 EU/mL, at least about 0.12 EU/mL, at least about 0.14 EU/mL, at least about 0.15 EU/mL, at least about 0.18 EU/mL, at least about 0.20 EU/mL, at least about 0.25 EU/mL, at least about 0.30 EU/mL, at least about 0.32 EU/mL, or at least about 0.34 EU/mL. As a further example, in some embodiments, actions may be triggered by an endotoxin quantity that is greater than the quantity needed to trigger an alert, such as at least about 0.05 EU/mL, at least about 0.08 EU/mL, at least about 0.1 EU/mL, at least about 0.15 EU/mL, at least about 0.20 EU/mL, at least about 0.25 EU/mL, at least about 0.28 EU/mL, at least about 0.30 EU/mL, at least about 0.35 EU/mL, at least about 0.40 EU/mL, at least about 0.45 EU/mL, at least about 0.5 EU/mL, at least about 0.8 EU/mL, at least about 0.85 EU/mL, or at least about 0.90 EU/mL.

In some aspects, process 100 (and other systems and methods disclosed herein) may be implemented as part of an in-process control system, which may operate within the framework of an organization's quality system to ensure consistency and adherence to internal and/or external safety requirements. As a part of such a program, data regarding the presence and/or quantity of endotoxins in filters may be collected and reviewed (e.g., digitally by a computer and/or manually by a human) in real-time or close to real-time, allowing preventative and/or corrective actions to be taken. Preventative and/or corrective actions may be triggered by, e.g., a quantity of endotoxin exceeding a predetermined "action" level for one or more sample points during a screening, or a quantity of filters from a particular source failing to pass a screening test (e.g., exceeding a predetermined "action" or "alert" level of endotoxin detected during a process such as process 100). Preventative and/or corrective actions may include, e.g., cleaning or discarding a plurality of filters associated with a filter being screened, finding a new source of naturally-sourced materials for a filter lot, or obtaining filters from a new filter vendor.

In some embodiments, steps 102, 104, and 106 of process 100 may be performed to, e.g., clean one or more filters from a plurality of filters. This may be done, e.g., as a response to detection of endotoxin in a filter from the plurality of filters.

FIG. 2 depicts, in flow-chart form, an exemplary process 200 for determining suitability of a buffer solution for use in an endotoxin detection process according to the present disclosure. One of ordinary skill in the art will understand that many variations to this process are suitable. According to step 202, a buffer solution may be passed through a first filter of a filter lot. According to step 204, purified water, e.g., water for injection (WFI), may be passed through the first filter. According to step 206, the buffer solution and the WFI may be assayed for a quantity of endotoxin. According to step 208, cell culture fluid may be passed through a second filter of the filter lot at the same time as, before, or after, steps 202, 204, and 206. According to step 210, the cell culture fluid passed through the second filter may be assayed for a quantity of endotoxin. According to step 212, the quantity of endotoxin detected in the buffer solution and/or the WFI (per step 206) may be compared with the quantity of endotoxin detected in the cell culture fluid (per step 210).

According to step 202, a buffer solution may be passed through a first filter of a filter lot. The buffer solution may be selected based on characteristics of the buffer solution, including, e.g., characteristics that may allow the buffer solution to disrupt interactions between a filter and endotoxins in the filter. Similarly, a volume of the buffer solution may be selected based on an estimated or hypothesized volume sufficient to remove endotoxins from the filter.

According to step 204, purified water, e.g., water for injection (WFI), may be passed through the first filter. As with the buffer solution, a volume of WFI may be selected based on an estimated or hypothesized volume sufficient to wash endotoxins from the filter. In some embodiments, a conductivity gradient may form between the WFI and residual buffer solution trapped in the filter, upon introduction of the WFI to the filter. Without intending to be bound by theory, it is believed that such a conductivity gradient may assist in disrupting electrostatic interactions between endotoxins and the first filter.

According to step 206, samples of the buffer solution and the WFI that have passed through the filter may be assayed for a quantity of endotoxin. Each sample may be assayed separately, or in some embodiments, samples may be combined and assayed together. Any suitable assay, now known or future developed, may be used to determine the presence and/or quantity of endotoxin. For example, a LAL assay (or LAL-based assay), a fluorescent assay, or a recombinant factor C assay may be used. In some embodiments, a LAL KTA is used.

According to step 208, cell culture fluid may be passed through a second filter of the filter lot. As has been previously discussed, because of the variety of molecules typically present, cell culture fluid may be capable of interacting with endotoxins and/or disrupting bonds or other interactions between endotoxins and filter media. In some embodiments, the volume of cell culture fluid used for the second filter in step 208 may be comparable to the volume of buffer solution used for the first filter in step 202 and/or the volume of WFI used for step 204.

According to step 210, the cell culture fluid passed through the second filter may be assayed for a quantity of endotoxin. The type of assay used for this step, and the assaying process, may be the same as the assay used in step 206. In this manner, the quantity of endotoxin detected in the cell culture fluid may serve as a reference point for evaluating the effectiveness of the buffer solution/WFI in removing endotoxin from the first filter as an representative filter of the filter lot.

According to step 212, the quantity of endotoxin detected in the buffer solution and/or the WFI may be compared with the quantity of endotoxin detected in the cell culture fluid. Comparable quantities of detected endotoxins in the buffer solution/WFI as detected in the cell culture fluid, or greater quantities of detected endotoxin in the buffer solution/WFI as compared to that detected in the cell culture fluid, may indicate that the buffer solution is suitable for use as an endotoxin screening tool in depth filters. In some embodiments, instead of cell culture fluid, a buffer solution with properties suitable for screening filters for endotoxins in accordance with the present disclosure may be used in steps 208, 210, and 212.

Examples

The following examples are intended to illustrate the present disclosure without, however, being limiting in nature. It is understood that the present disclosure encompasses additional aspects and embodiments consistent with the foregoing description and following examples.

Example 1

Multiple buffer solutions (Buffers 1-4) were evaluated for their ability to extract endotoxins from depth filters. The evaluated buffer solutions were chosen based on their potential to disrupt both electrostatic and hydrophobic interactions between endotoxins and the depth filter media. The buffer solutions, some of their properties, and the filters with which the buffer solutions were tested, are listed in Table 1 below ("Tris" refers to tris(hydroxymethyl)aminomethane).

TABLE 1

Buffer candidates for endotoxin screening of depth filters

| Buffer Composition | Buffer pH | Buffer Conductivity, mS/cm | Depth Filter Screened |
|---|---|---|---|
| Buffer 1: 10 mM Na-Phosphate, 0.5M NaCl | 7.1-7.3 | 40-50 | Depth Filter A and Depth Filter B |
| Buffer 2: 40 mM Tris, 250 mM citrate, 35 mM NaCl | 8.4-8.6 | 33.0-38.5 | Depth Filter A |
| Buffer 3: 50 mM Tris, 120 mM sodium citrate | 8.2-8.4 | 19-24 | Depth Filter B |
| Buffer 4: 25 mM histidine, 25 mM arginine | 5.6-6.0 | 3-4 | Depth Filter A |

Depth filter endotoxin screening was performed on two different types of depth filters (designated Depth Filter A and Depth Filter B) using the buffer solutions listed in Table 1. Each depth filter was subjected to a WFI pre-rinse stage, followed by a stage in which each depth filter was loaded and flushed by one of the buffer solutions. Loading and flux of the buffer in each filter corresponded to settings used in large-scale production (about 100-125 L/m$^2$ at 84 L/m$^2$/hr (LMH)). The buffer flush of each depth filter was followed by a secondary WFI rinse stage. Samples of each WFI rinse stage and the buffer flushing stage were caught at about 25 L/m$^2$ intervals (i.e., 25 L/m$^2$ of fluid was allowed to flow between samples) and were assayed for presence and quantity of endotoxin, using the Limulus amebocyte lysate (LAL) kinetic turbidimetric assay (KTA).

Figure 3:
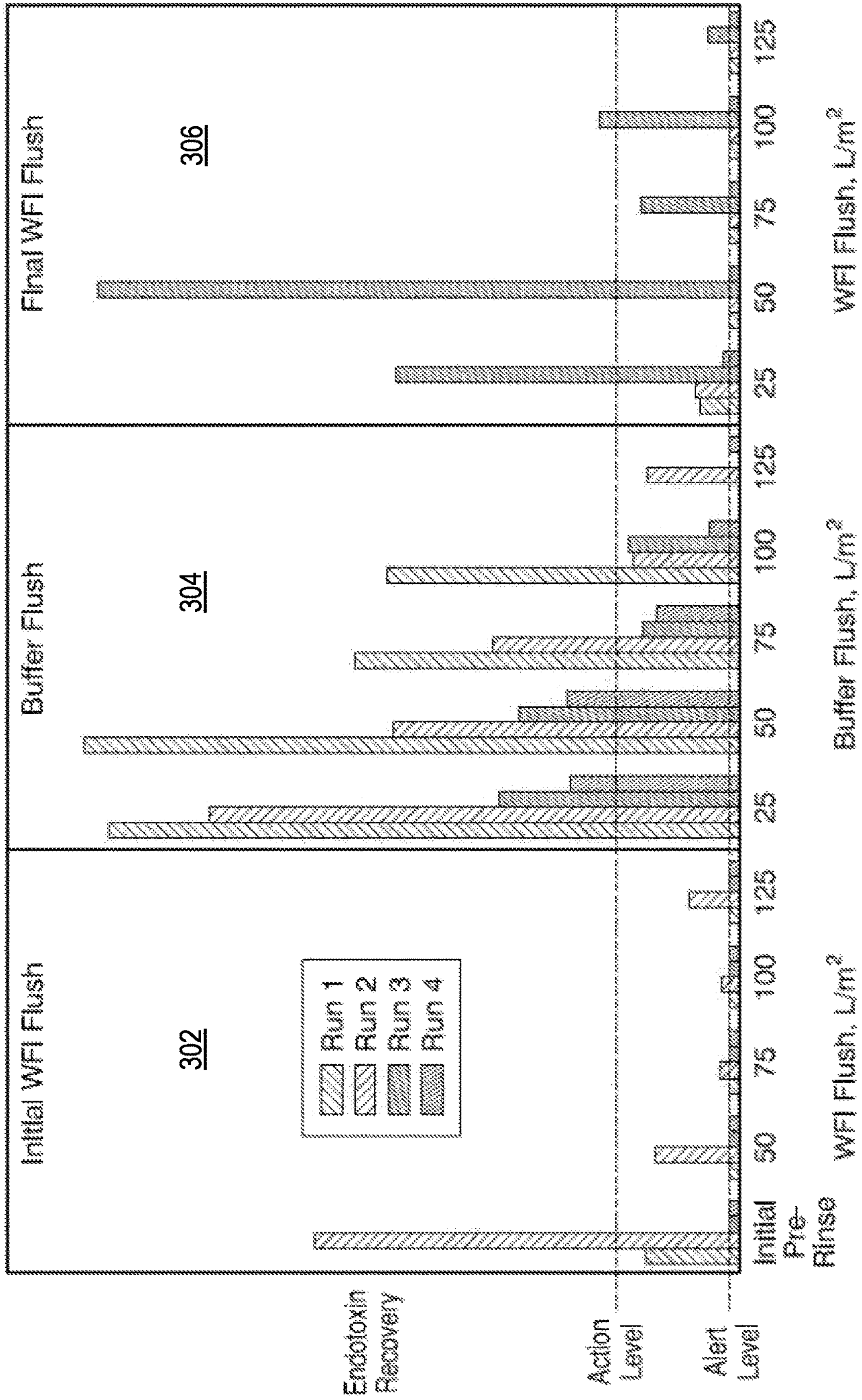
FIG. 3 depicts a graph of endotoxin recovery during a process of flushing filters with water for injection (WFI) and various buffers as described in Example 1.

FIG. 3 depicts a graph 300 of endotoxin recovery, as shown using the LAL KTA on the catch samples. The dashed horizontal lines across the graph show "Alert" and "Action" endotoxin limits specified for operation of the harvest unit in which the depth filters were screened, and the solid vertical lines identify the initial WFI flush (panel 302), the flush with respective buffer solutions (panel 304), and the final WFI flush (panel 306). Run 1 corresponds to the use of Buffer 1 (as described in Table 1 above) in screening Depth Filter A. Run 2 corresponds to the use of Buffer 1 in screening Depth Filter B. Run 3 corresponds to the use of Buffer 2 (as described in Table 1) in screening Depth Filter A. Run 4 corresponds to the use of Buffer 3 (as described in Table 1) in screening Depth Filter A. The run including Buffer 4 did not result in any detectable recovery of endotoxin (the minimum detectable quantity was 0.05 EU/mL), and is therefore not depicted on the graph. On this basis, it was concluded that a buffer solution of histidine/arginine was less successful than the other buffer solutions tested in the removal of endotoxins.

The results indicate that the initial WFI pre-use rinse did not generally remove significant amounts of endotoxin from the depth filter. As shown in FIG. 3, Runs 1 and 2 exhibited heightened endotoxin detection in the WFI pre-rinse stage (particularly Run 1). It is hypothesized that the depth filter used in this run contained extractables that could have interfered with the LAL assay. However, there was a significant increase in amount of endotoxin extracted from the depth filters when Buffer 1 was used (Runs 1 and 2). As depicted in FIG. 3, the highest endotoxin levels were detected as early as 25 L/m$^2$ into the buffer flush (panel 304 in FIG. 3) of Runs 1 and 2. Data for Buffers 2 and 3 (Runs 3 and 4) also exhibited the extraction of significant amounts of endotoxin from the depth filters. In Run 3 (corresponding to the use of Buffer 2), additional endotoxin was removed from the depth filter by the secondary WFI rinse, indicating that including a secondary WFI rinse in a screening process may, in some cases, be beneficial. Notably, the use of Buffer 2 (Run 3) resulted in higher endotoxin levels appearing in the secondary WFI rinse step than in the buffer flush step. One possible cause of this may be the generation of a conductivity gradient within the depth filter upon the introduction of the secondary WFI rinse, facilitating better removal of endotoxin.

Based on these results, Buffer 1 (10 mM Na-phosphate, 0.5M NaCl) was determined to be one useful buffer solution for screening lots of depth filters for the presence and/or quantity of endotoxins.

Example 2

Buffer 1 (10 mM Na-phosphate, 0.5M NaCl) was used to screen 14 depth filter lots for the presence of endotoxins, and to identify depth filter lots having a risk of releasing endotoxins during protein harvesting operations. A depth filter from each of the 14 lots was selected for screening. Each of the 14 selected depth filters was washed with a volume of about 110 L/m$^2$ of Buffer 1, at a rate of 84 LMH. Samples of the wash were taken at 20, 40, 60, 80, 90, 100, and 110 L/m$^2$ and were subjected to LAL KTA.

Figure 4:
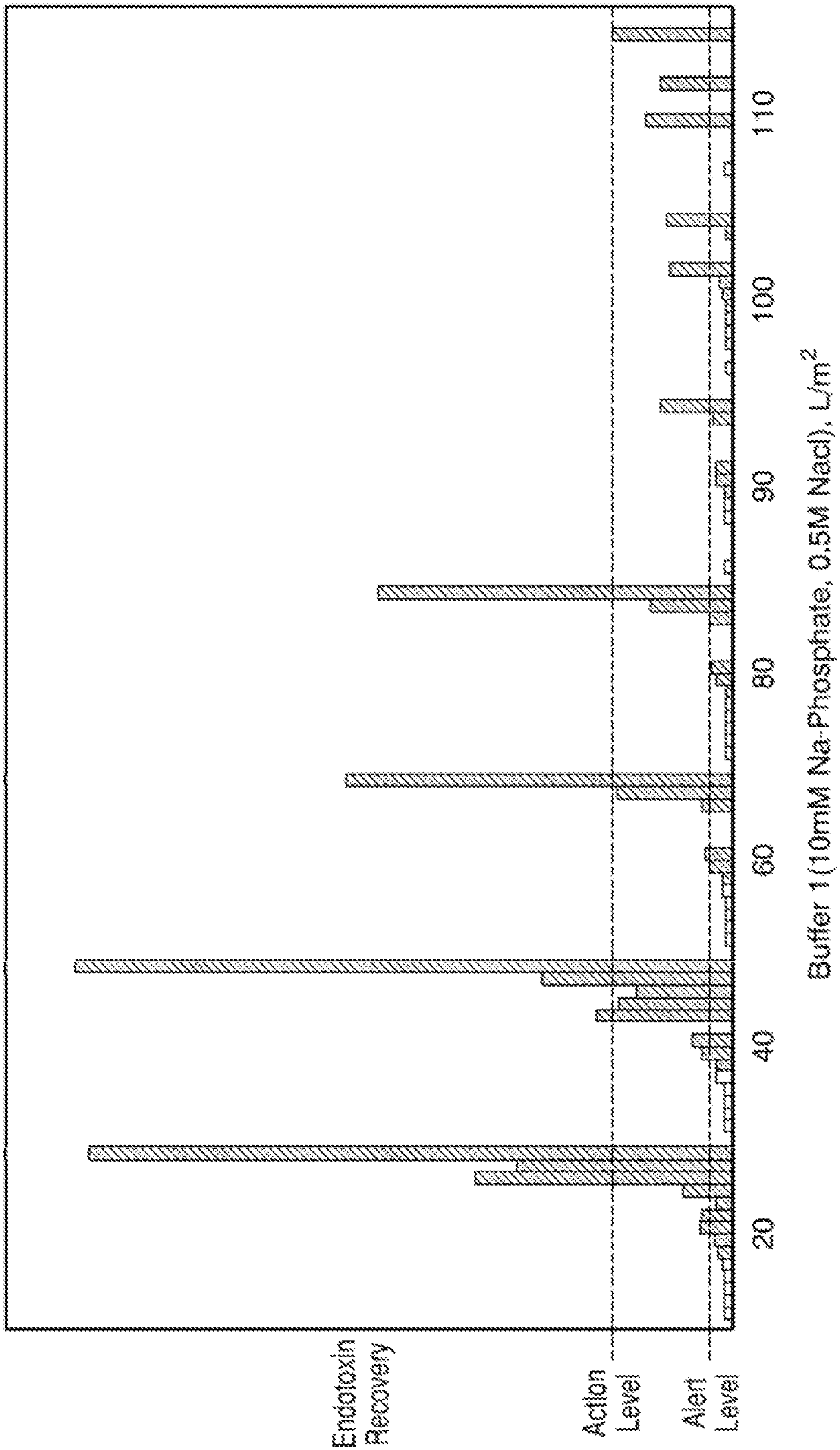
FIG. 4 depicts a graph of endotoxin recovery during a process of flushing filters with a sodium phosphate buffer as described in Example 2.

FIG. 4 depicts a graph 400 of the results of the LAL KTA for each selected filter at each sample point. As with FIG. 3, "Alert" and "Action" endotoxin levels specified for operation of the harvest apparatus are depicted using a dotted line. Missing bars for a sample point indicate that there was no detectable endotoxin in the buffer wash for that selected filter at that sample point. Out of the 14 selected depth filters, five filters (shown as solid white bars) did not exhibit "Alert" levels of endotoxin at any sample point during the screening. The remaining filters (shown by striped bars) did exhibit at least an "Alert" level of endotoxin at one sample point (or more) during the screening. It was concluded that the filter lots of those five filters were likely to be considered acceptable for manufacturing-scale protein harvest operations.

Those skilled in the art will appreciate that the conception upon which this disclosure is based may readily be used as a basis for designing other methods and systems for carrying out the several purposes of the present disclosure. Accordingly, the claims are not to be considered as limited by the foregoing description.

What is claimed is:

1. A method, comprising:

selecting a filter from a plurality of filters, wherein each of the plurality of filters comprises cellulose and/or diatomaceous earth;

passing a volume of a buffer solution through the selected filter, wherein the buffer solution is configured to remove endotoxins from the selected filter, and wherein the buffer solution has a conductivity of at least about 40 mS/cm at 25° C. when tested in accordance with ASTM D1125;

performing an assay of the buffer solution passed through the selected filter to detect a presence of an endotoxin removed from the selected filter; and evaluating a suitability of the plurality of filters based on a result of the assay.

2. The method of claim 1, wherein the evaluating step includes:

approving the plurality of filters for use in a biologic purification process based on a quantity of endotoxin in the buffer solution passed through the selected filter being below a first predetermined threshold; or rejecting the plurality of filters for use in a biologic purification process based on the quantity of endotoxin in the buffer solution passed through the selected filter being above a second predetermined threshold.

3. The method of claim 2, wherein the first predetermined threshold is at least about 0.34 EU/mL.

4. The method of claim 2, wherein the second predetermined threshold is at least about 0.90 EU/mL.

5. The method of claim 1, wherein the buffer solution comprises sodium phosphate.

6. The method of claim 1, further comprising:

repeating the selecting, passing, performing, and evaluating steps at periodic time intervals.

7. A method, comprising:

contacting a naturally-sourced material with a buffer solution, wherein the naturally-sourced material comprises cellulose and/or diatomaceous earth, wherein the buffer solution is configured to remove an endotoxin from the naturally-sourced material, and the buffer solution has a conductivity of at least about 40 mS/cm at 25° C. when tested in accordance with ASTM D1125; and performing an assay of the buffer solution to detect a presence of the endotoxin removed from the naturally-sourced material in the buffer solution.

8. The method of claim 7, further comprising:

after contacting the naturally-sourced material with the buffer solution, contacting the naturally-sourced material with a cell culture fluid.

9. The method of claim 7, wherein the buffer solution comprises tris(hydroxymethyl)aminomethane, citrate, histidine, arginine, phosphate and/or mixtures thereof.

10. The method of claim 7, wherein the step of contacting the naturally-sourced material with a buffer solution comprises passing at least 25 $L/m^2$ of the buffer solution through a filter that comprises the naturally-sourced material.

11. The method of claim 7, further comprising:

after contacting the naturally-sourced material with the buffer solution, contacting the naturally-sourced material with water for injection (WFI); and performing an assay on the WFI to detect the endotoxin in the WFI.

12. A method comprising:

passing a buffer solution through a first filter of a filter lot, the filter lot including a plurality of filters comprising naturally-sourced materials, and the buffer solution is configured to remove an endotoxin from the first filter;

assaying the buffer solution passed through the first filter to detect a quantity of the endotoxin removed from the first filter and present in the buffer solution;

passing a cell culture fluid through a second filter of the filter lot;

assaying the cell culture fluid passed through the second filter to detect a quantity of the endotoxin removed from the second filter and present in the cell culture fluid; and comparing the quantity of the endotoxin detected in the buffer solution to the quantity of the endotoxin detected in the cell culture fluid, wherein the naturally-sourced materials include one of cellulose and/or diatomaceous earth.

13. The method of claim 12, wherein the buffer solution comprises tris(hydroxymethyl)aminomethane, citrate, histidine, arginine, and/or mixtures thereof.

14. The method of claim 13, wherein the buffer solution has a conductivity of at least about 40 mS/cm at 25° C. when tested in accordance with ASTM D1125.

15. The method of claim 12, wherein assaying the cell culture fluid comprises assaying a clarified pool of the cell culture fluid.

16. The method of claim 12, further comprising:

determining a threshold quantity of endotoxin, wherein the threshold quantity of endotoxin includes the quantity of the endotoxin detected in the cell culture fluid passed through the second filter; and approving the buffer solution for use in the endotoxin detection process based on the quantity of the endotoxin detected in the buffer solution passed through the first filter being above the threshold quantity.

17. A method comprising:

passing a buffer solution through a filter, wherein the buffer solution is configured to remove endotoxins from the filter, thereby washing endotoxins from the filter before use, and assaying the buffer solution passed through the filter to determine a quantity of endotoxin in the buffer solution, wherein the buffer solution comprises tris(hydroxymethyl)aminomethane, citrate, histidine, arginine, or a combination thereof, and has a conductivity of at least about 40 mS/cm at 25° C. when tested in accordance with ASTM D1125;

wherein the filter is a harvest depth filter, the harvest depth filter comprises naturally-sourced materials and the naturally-sourced materials comprise cellulose and/or diatomaceous earth.

18. The method of claim 17, further comprising:

after passing the buffer solution through the filter, passing a volume of cell culture fluid through the filter.

19. The method of claim 17, wherein the buffer solution further comprises sodium phosphate at a concentration of about 10 mM.

* * * * *